(12) United States Patent
Schäfer

(10) Patent No.: US 10,639,409 B2
(45) Date of Patent: May 5, 2020

(54) PERISTALTIC PUMP COMPRISING MODULAR CASING

(71) Applicant: B. BRAUN AVITUM AG, Melsungen (DE)

(72) Inventor: Oliver Schäfer, Neuenstein (DE)

(73) Assignee: B. Braun Avitum AG (DE)

( * ) Notice: Subject to any disclaimer, the term of this patent is extended or adjusted under 35 U.S.C. 154(b) by 537 days.

(21) Appl. No.: 15/664,403

(22) Filed: Jul. 31, 2017

(65) Prior Publication Data

US 2018/0043073 A1    Feb. 15, 2018

(30) Foreign Application Priority Data

Aug. 11, 2016  (DE) ........................ 10 2016 114 958

(51) Int. Cl.
| | |
|---|---|
| *A61M 1/10* | (2006.01) |
| *A61M 1/16* | (2006.01) |
| *A61M 1/36* | (2006.01) |
| *A61B 5/00* | (2006.01) |

(52) U.S. Cl.
CPC ........ *A61M 1/1006* (2014.02); *A61M 1/1039* (2014.02); *A61M 1/1645* (2014.02); *A61B 5/6866* (2013.01); *A61M 1/3601* (2014.02)

(58) Field of Classification Search
CPC . A61B 5/6866; A61M 1/1039; A61M 1/1645; A61M 1/3601; A61M 1/1006
See application file for complete search history.

(56) References Cited

U.S. PATENT DOCUMENTS

| | | |
|---|---|---|
| 4,558,996 A | 12/1985 | Becker |
| 5,044,902 A | 9/1991 | Malbec |
| 2010/0129248 A1 | 5/2010 | Mou |
| 2010/0278667 A1 | 11/2010 | Gault et al. |
| 2012/0294742 A1 | 11/2012 | Reich et al. |

(Continued)

FOREIGN PATENT DOCUMENTS

| | | |
|---|---|---|
| DE | 19745999 A1 | 4/1999 |
| DE | 102010000594 A1 | 9/2011 |

(Continued)

OTHER PUBLICATIONS

Extended European Search Report for European Application No. 17184560.5, dated Jan. 2, 2018, including English translation, 13 pages.

(Continued)

*Primary Examiner* — Leslie R Deak

(74) *Attorney, Agent, or Firm* — RatnerPrestia

(57) ABSTRACT

A peristaltic pump for an apparatus for extracorporeal blood treatment, especially for a dialysis machine, for delivering fluid in the apparatus is disclosed. The peristaltic pump includes a rotor driven to rotate about a rotor axis and a pump casing surrounding the rotor at least in part and including a supporting surface being configured to be curved around the rotor axis, wherein an elastically deformable fluid line is adapted to be positioned between the rotor and the supporting surface and is deformed between the rotor and the supporting surface while forming a cross-sectional constriction for fluid delivery by rotation of the rotor, the pump casing having a modular design and including a supporting surface module forming the supporting surface and a casing module adapted to be coupled to the former and surrounding the rotor at least in part.

13 Claims, 3 Drawing Sheets

(56) References Cited

U.S. PATENT DOCUMENTS

2013/0045121 A1    2/2013   Rodau et al.
2013/0317408 A1   11/2013   Schade

FOREIGN PATENT DOCUMENTS

| DE | 102012104461 A1 | 12/2013 |
|----|-----------------|---------|
| EP | 2397695 A1 | 12/2011 |
| WO | 9710436 A2 | 3/1997 |
| WO | 2010090944 A1 | 8/2010 |
| WO | 2010093946 A1 | 8/2010 |
| WO | 2012162512 A1 | 11/2012 |

OTHER PUBLICATIONS

German Search Report for German Application No. 10 2016 114 958.6, dated Feb. 24, 2017, with translation—13 Pages, 2017.

PERISTALTIC PUMP COMPRISING MODULAR CASING

CROSS REFERENCE TO RELATED APPLICATIONS

This application claims priority to German application DE 10 2016 114 958.6 filed Aug. 11, 2016, the contents of such application being incorporated by reference herein.

FIELD OF THE INVENTION

The invention relates to a peristaltic pump for an apparatus for extracorporeal blood treatment, especially for a dialysis machine, for delivering fluid in the apparatus and, respectively, in the dialysis machine, said peristaltic pump comprising a rotor being rotatable about a rotor axis and a pump casing surrounding the rotor at least in part and having a supporting surface formed to be curved about the rotor axis, wherein an elastically deformable fluid line can be or is positioned between the rotor and the supporting surface and while forming a cross-sectional constriction for delivering fluid by rotation of the rotor is deformed between the rotor and the supporting surface.

BACKGROUND OF THE INVENTION

Known peristaltic pumps in medical apparatuses for extracorporeal blood treatment usually comprise a rotor, a pump casing and an elastic hose line arranged between the rotor and the pump casing as a fluid line. The pump casing usually is configured in one piece and, apart from other functions such as e.g. formation of fluid lines and connectors, fixtures for sensors and covering/shielding of particular parts of the pump from the environment, forms a supporting surface for the fluid line. From the state of the art attached blood pump casings are known, for example configured as a separate milled aluminum part or plastic injection molded part and mounted on a housing front of the apparatus.

DESCRIPTION OF THE RELATED ART

Further, from the state of the art multi-part pump casings are known, for example from WO 2012/162512 A1 or from EP 2 397 695 A1 which discloses a tube pump comprising a casing having a cylindrical side wall in an inner portion thereof as well as a holder for connecting portions for fluid lines adapted to be coupled to the casing. The pump further comprises a rotor having a roller which is disposed on an inside of the cylindrical side wall of the casing, wherein the rotor is rotated by a drive source. The tube pump comprises a line having a curved portion for attachment between the cylindrical side wall and the roller. The tube pump is configured for rotating the rotor so as to pinch the curved portion via the roller, thus causing fluid to be pumped through the line, wherein a first connecting portion is provided on the inlet side and on the outlet side. The holder includes second connecting portions for connection to the first connecting portions of the line, the second connecting portions being engaged in the first connecting portions of the line so as to hold the line. Although such multi-part pump casings consist of plural parts coupled and connected to one another, said parts are not replaceable for similar but not identical parts. Especially, no modular concept of multi-part pump casings is known in which different modules can be exchanged and combined with others and replaced for different ones. It can also be stated that it is not known from the state of the art to realize uniformity of components with varying shapes of casings.

From DE 10 2010 000 594 A1 a tube pump for delivering a medium guided in a tube comprising plural pinch elements which force the tube against a counter-bearing while pinching the same and in this way deliver the medium inside the tube in the delivery direction. In order to enable the tube to be easily and quickly inserted in such tube pump, the tube pump has a threading means for inserting the tube between the pinch elements and the counter-bearing.

From DE 10 2012 104 461 A1 a medical apparatus for extracorporeal blood treatment is known comprising an extracorporeal blood circulation including a tube and two sensor units measuring on the tube by different functioning principles to which portions of the tube can be coupled for measurement, wherein each sensor unit consists of a sensor-specific component and a sensor-neutral component, the sensor-neutral components of the sensor units being identical, while the sensor-specific components differ from each other depending on the functioning principle and each comprises a specific sensor system, and wherein for each sensor unit a sensor-neutral component is mounted on a sensor-specific component, with a portion of the tube being adapted to be coupled to the sensor system of the sensor-specific component located there beneath when it is introduced to and fixed in a sensor-neutral component so that measurement can be carried out on the tube by the sensor system.

In known systems, it is a drawback that different functional elements or geometries of the casing are realized by one single or with one single component, especially in the form of a one-part casing. It can also be stated that known casings have to fulfill a plurality of functions such as forming the supporting or running surface along with forming a particular exterior design or appearance of the pump or holding functions for feed and drain lines or simple cover functions. In this way, the use of existing pumps in other apparatus variants is not or only restrictedly possible due to a fixed outer design. It is impossible, as a rule, to use a particular known pump having a particular pump characteristic which may be substantially defined by parameters of the supporting surface with a different cover or on a different machine having different connecting options of the pump.

SUMMARY OF THE INVENTION

Based on the afore-described state of the art, an object underlying the present invention is to eliminate the afore-listed drawbacks, especially to provide a peristaltic pump for an apparatus for extracorporeal blood treatment, especially for a dialysis machine, which enables high variability of the exterior pump design with constant functional structure and/or higher variability as regards the pump characteristic while the pump design is unchanged and development costs are low.

In accordance with the invention, this object is achieved by a peristaltic pump for an apparatus for extracorporeal blood treatment, especially for a dialysis machine, for conveying fluid in the apparatus, wherein the peristaltic pump includes a rotor rotatably driven about a rotor axis and a pump casing at least partially surrounding the rotor and having a supporting surface configured to be curved around the rotor axis, wherein an elastically deformable fluid line is adapted to be positioned (removably positioned) between the rotor and the supporting surface and is (continuously) deformed between said rotor and the supporting surface while forming a cross-sectional constriction for fluid delivery by rotation of the rotor, with the pump casing having a modular design such that it includes a supporting surface module forming the supporting surface and a casing/cover module adapted to be coupled therewith and at least partially surrounding the rotor.

More generally speaking, the pump casing has at least two casing modules adapted to be coupled to each other, i.e. a first module adapted to encompass or enclose/receive the rotor and a second module adapted to provide a supporting surface for a flexible/pinchable fluid line inserted in the same against which the fluid line can be pressed with the rotor while forming fluid receiving chambers in the fluid line. In this way, the first module can be designed independently of the second module, wherein differently designed first modules can be combined at will with the second module.

An object is further achieved by an apparatus for extracorporeal blood treatment (extracorporeal blood treatment machine/dialysis machine) comprising a peristaltic pump according to aspects of the invention, especially as disclosed in the present description or as claimed in the attached claims.

The invention thus relates to a casing of modular design of a blood pump, especially a peristaltic pump, wherein the functions of the casing are split into different function modules. The different modules according to aspects the invention especially may be the supporting surface module (main functional module of running surface) which co-defines the delivery volume by its cylindrical radius and its wrap angle of the supporting surface, as well as the housing module (functional module of screen or design cover) defining the outer appearance of the pump.

The casing module may realize further functions and functional elements, such as, for example, forming a tube adapter, receiving and enclosing sensors, incorporating cover adapters etc.

The casing module may serve especially for guiding and/or holding a transition system in the form of the elastically deformable fluid line, for example. The individual modules may especially belong to a set of appropriate modules.

The peristaltic pump of the apparatus according to aspects of the invention may usually deliver a defined volume of a medium, such as e.g. blood or dialysis solution, from a low-pressure side, usually the arterial side, to a high-pressure side, usually the venous side. The elastic fluid line is inserted in the same in loop shape between the rotor and the supporting surface formed by the supporting surface module. It may be guided or held especially by the casing module. The rotor and the supporting surface supporting the elastic fluid line are configured and adjusted to each other such that a delivery path is formed therebetween. In the course thereof, the elastically deformable fluid line is deformed and pinched off upon rotation of the rotor about the rotor axis. The rotor is configured so that the fluid line is pinched only locally or in portions. For example, it may include pinching elements biased against the fluid line and/or adapted to be positioned relative to the rotor axis. The pinching point caused by the contact with the rotor migrates along with the rotating rotor and is moved so-to-speak through the fluid line from the low-pressure side to the high-pressure side. As a consequence, fluid is forced out of the fluid line in the delivering direction. Re-supplied fluid is sucked into the line by low pressure, especially vacuum, which is formed due to elastic re-forming of the fluid line after deformation by the rotor. The elastically deformable fluid line may be a tube, for example.

Especially the following advantages can be achieved by the invention:

By making use of the basic division of functions according to aspects of the invention by providing plural functional modules it may concretely allowed for the fact that main functional modules of a blood pump which form or contain the supporting or running surfaces have to be developed and qualified only once (to be universally usable) and during further use are adapted to be combined via standardized interfaces with other different functional modules such as one or more casing modules and/or one or more mounting modules (to be individually usable).

This enables the different modules to be repeatedly in different combinations on various machines in different marginal conditions. Development times and qualification costs may be advantageously reduced.

By splitting functions and the association thereof with separate functional modules high variation is possible with same parts that are critical as to function.

Plural variants can be fabricated with identical same parts, which results in a reduction of costs for the apparatus variants.

Advantageous embodiments of the invention are claimed in the subclaims and shall be illustrated in detail hereinafter.

One embodiment of the peristaltic pump is that the pump casing further includes a mounting module. The latter may be configured either as a separate component or as part of a casing of an apparatus for extracorporeal blood treatment, especially an apparatus front. The mounting module may especially be adapted to be coupled or may be coupled, on the one hand, to the supporting surface module and/or to the casing module. On the other hand, it may be adapted to be coupled or may be coupled, also directly, to the apparatus for extracorporeal blood treatment, especially to the casing thereof.

Preferably, the supporting surface module may comprise at least one standardized interface for coupling to the casing module and/or to the mounting module and/or to a casing element of the apparatus. Coupling in this context comprises, for example, arranging, fixing or fastening said modules with or to each other. It is of particular advantage when the peristaltic pump according to one embodiment includes a casing module having a standardized interface for coupling to the supporting surface module and/or the mounting module and/or a casing element of the apparatus. Also, the mounting module may have a standardized interface for coupling to the supporting surface module and/or the casing module and/or to a casing element of the apparatus. The modules can be easily combined and coupled via said interfaces. In this way, a particular module of a set of modules, for example a supporting surface module having a first supporting surface diameter, can be easily replaced with a different module of the set of modules, for example for a supporting surface module having a second supporting surface diameter, wherein the residual modules, i.e. the casing module and a possible present mounting module, may remain unchanged.

According to aspects of the invention, especially a plurality of supporting surface modules may be provided, for example in the form of a set or module set. The individual modules of the set may differ from each other especially as regards the radius of their supporting surface and/or as regards the wrapping angle formed by the supporting surface. Similarly, according to aspects of the invention a plurality of casing modules may be provided which differ from one another as regards particular characteristics, such as especially the fluid line adapter, the equipment with sensors, the cover adapter and/or the design.

It is especially advantageous when the supporting surface module is an extruded element or a deep-drawn element or is designed by cold forming. It may be made especially from metallic material or from plastic material. Such modules can be manufactured in a simple and low-cost manner. Said supporting surface module may as well be an extruded plastic component, an injection molded part or a mechanically machined part (tube, plate etc.).

According to one embodiment of the invention, the mounting module may be a separate component. Alternatively, it may be part of a casing of the apparatus, in particular an apparatus front of the apparatus casing. In this way, a peristaltic pump according to aspects of the invention can be easily utilized together with existing apparatuses for extracorporeal blood treatment. Moreover, it may be removed from one type of machine and may be arranged and used on a different type of machine in an especially simple and efficient manner.

According to one embodiment, the supporting surface is designed by cold forming, especially by deep drawing, in the machine casing, especially in a sheet metal part forming the machine front. The configuration of the supporting surface thus may be easily integrated in a common process of manufacturing the machine casing or at least of parts thereof.

According to one embodiment, the supporting surface module of a pump may be a standard for an apparatus platform. Depending on the equipment of the machine (for example in a high-quality "high-end" version, in a standard version or in a budget version), said supporting surface module may be equipped or combined with different casing modules which may also be referred to as functional module of casing, e.g. with a high-end screen, a standard screen or a budget screen. In other words, the respective machine variant comprising a standard supporting surface module may be defined by an appropriate combination with corresponding casing modules (or mounting modules). Accordingly, the functional modules may have most various additional functions in accordance with the respective equipment features.

It can also be stated that the invention relates to a casing of a blood pump which is part of a roller pump operating in a peristaltic manner, especially a tube pump for medical engineering. The pump may have its intended use especially in the extracorporeal blood treatment, for example. A rotor permits, along with elastic material properties of a pump segment of a tube system, for example in the form of an elastic tube, a pumping function ensuring, for example, blood delivery to a dialyzer. Accordingly, the pump segment of the tube system may be inserted in loop shape against a running surface or supporting surface of a functional module which may also be referred to as supporting surface module or running surface module. The supporting or running surface may influence the amount of medium delivered with its cylindrical diameter and its cylindrical wrapping angle. The functional module "supporting surface" may be manufactured of most different materials, such as metal or plastic material, and with most different fabrication processes, such as milling, extrusion molding, deep drawing, die casting, extruding, injection molding etc. The functional module "casing" (screen) may equally be made from most different materials, such as metal or plastic material, and may be manufactured with most different fabrication processes, such as milling, extrusion molding, deep drawing, die casting, extruding, injection molding etc. The functional module "mounting" (seat), too, may be made from most different materials, such as metal or plastic material, and may be manufactured with most different fabrication processes, such as e.g. milling, extrusion molding, deep drawing, die casting, extruding, injection molding etc.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
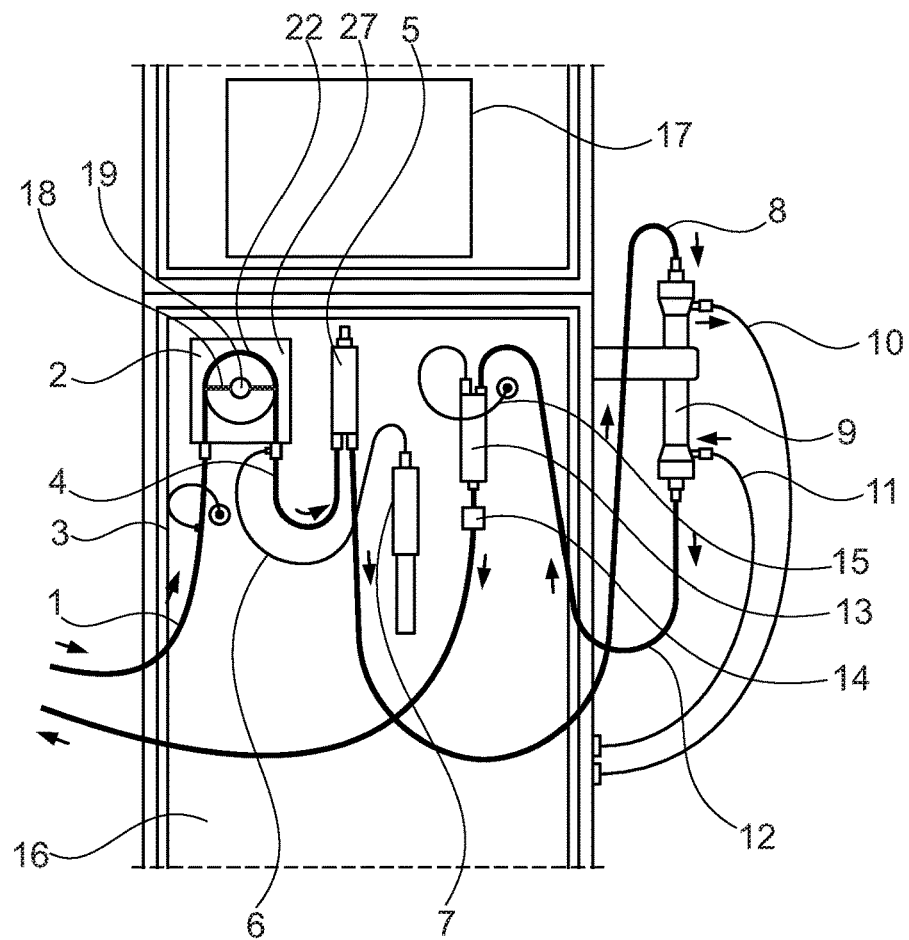
FIG. 1 is a schematic representation of a cutout from an apparatus for extracorporeal blood treatment.

FIG. 1 exemplifies a cutout from an apparatus for extracorporeal blood treatment according to aspects of the invention. There is substantially shown the entire extracorporeal blood circulation of the apparatus. The latter has an arterial blood line 1 with which blood is guided from a patient (not shown) to a peristaltic pump 2 of modular design of the treatment apparatus. Upstream of the peristaltic pump 2 an arterial pressure sensor 3 is provided for measuring the pressure upstream of the peristaltic pump 2, namely, the low-pressure side pressure. On the high-pressure side of the peristaltic pump 2 a high-pressure blood line 4 leads to an arterial blood collector 5. Directly at the outlet of the peristaltic pump 2 additive may be fed to the blood provided in the system with a feed line 6 and a pump 7, e.g. heparin for hemodilution.

From the arterial blood collector 5 a line 8 guides blood which is under high pressure but is untreated yet and loaded with waste materials to a dialyzer 9. On the inlet side, dialysis solution is supplied thereto via a dialysis solution feed line 10. In the dialyzer 9 blood is treated, e.g. purified, in a known manner with the dialysis solution. Used dialysis solution is removed from the dialyzer 9 via a dialysis solution drain 11 and is supplied to waste disposal or recycling (not shown). Treated blood is guided with a blood drain 12 from the dialyzer 9 to a venous air collector 13 where air is separated with an air trap 14. At the venous air collector 13 a venous pressure sensor 15 is provided by which the venous pressure, namely, the high-pressure side pressure, is detected. Treated blood is returned from the air trap 14 via a venous blood line 16 to the patient. In FIG. 1 also a unit 17 for monitoring and controlling the apparatus is shown. The apparatus for extracorporeal blood treatment is encapsulated by a housing 100 which is configured at least in part as a formed sheet metal part.

Figure 2:
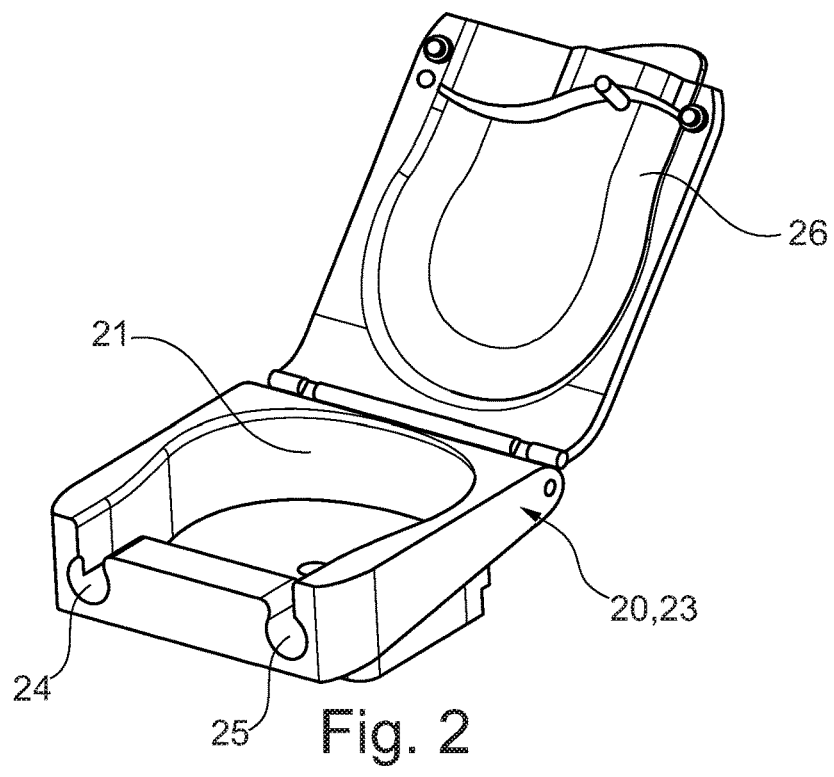
FIG. 2 is a schematic representation of a pump casing according to the state of the art.

FIG. 2 illustrates a blood pump casing 20 according to the state of the art. It is in the form of a separate milled aluminum part 23 adapted to be mounted onto the casing front 100 of the apparatus. The milled aluminum part 23 is relatively complex having an inlet groove 24 and an outlet groove 25 for the fluid line 22. The supporting surface 21 is formed in the milled aluminum part 23 by a milled recess entailing high material consumption. Moreover, a cover 26 is hinged on the casing 20 in a non-replaceable manner. If a different supporting surface contour or a different cover 26 is to be used, always the entire blood pump casing 20 has to be replaced.

The modular peristaltic pump 2 according to aspects of the invention includes a rotor 18 rotating about a rotor axis 19. The peristaltic pump 2 further includes a casing module 27 indicated in FIG. 1. The casing module 27 is shown together with a supporting surface module 28 adapted to be combined therewith and a mounting module 29 in FIG. 5 in a kind of exploded view. The casing module 27 configures a pump casing for the peristaltic pump 2 together with the supporting surface module 28 and the mounting module 29. Each of said three modules 27, 28, 29 may belong to a respective set of modules having different modules 27, 28, 29 in each case. According to aspects of the invention, all of said modules may be adapted to be combined with each other. This is achieved, inter alia, by the fact that the modules 27, 28, 29 have standardized interfaces enabling mutual coupling.

Figure 3:
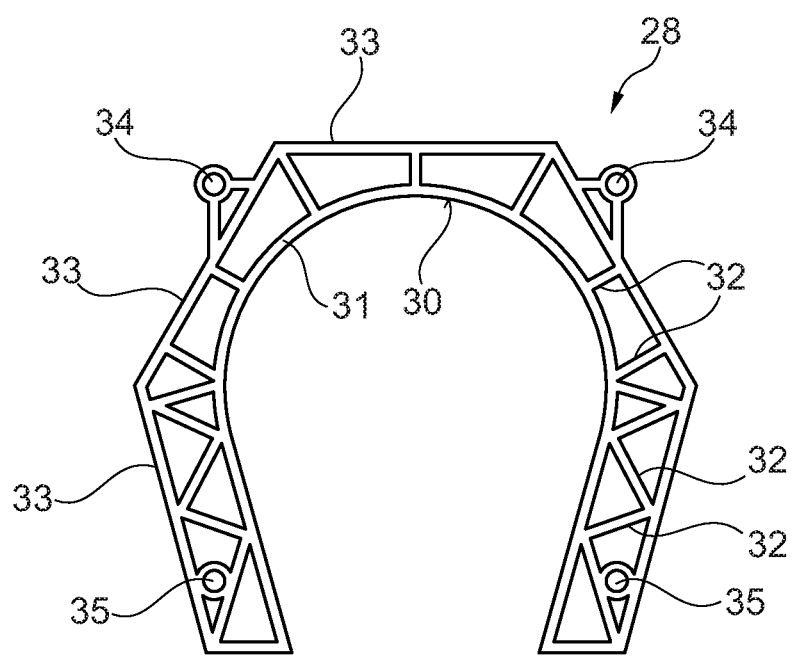
FIG. 3 is a schematic top view onto a supporting surface module of a peristaltic pump according to aspects of the invention.
Figure 4:
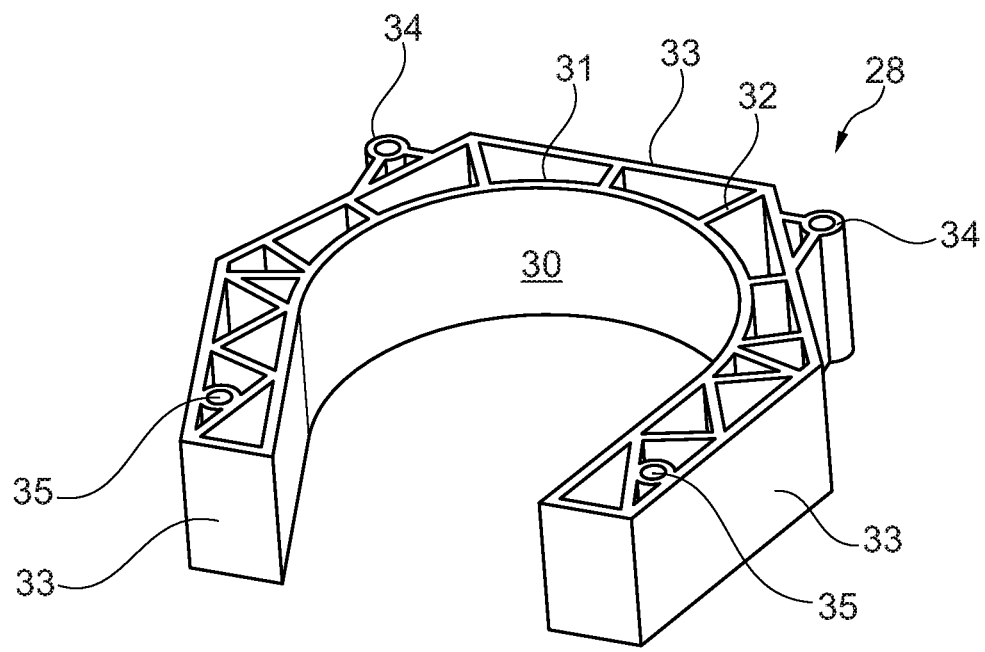
FIG. 4 shows the supporting surface module of FIG. 3 in a perspective view.

The interface of the supporting surface module 28 is evident especially clearly from FIGS. 3 and 4. The supporting surface module 28 is an extrusion-molded part having an integrated supporting surface 30. The latter is formed on an inner wall 31 bent in horse-shoe shape which is connected to an equally bent outer wall 33 via braces 32. On the outside of the outer wall 33 seats 34 for screws or bolts (not shown) are formed. Between the braces two further seats 35 for screws or bolts, which are not shown either, are arranged. The seats 34, 35 form an interface via which the supporting surface module 28 can be combined with and coupled to the casing module 27 and/or to the mounting module 29. In a set of supporting surface modules 28 a plurality of supporting surface modules 28 are contained which are different from each other as regards the curvature of the supporting surface 30, for example. The interfaces formed by the seats 34, 35 are always identical, however, so that each supporting surface module 28 of the set is adapted to be combined with and coupled to each casing module (of a set of casing modules, where appropriate) and/or mounting modules (of a set of mounting modules, where appropriate).

Figure 5:
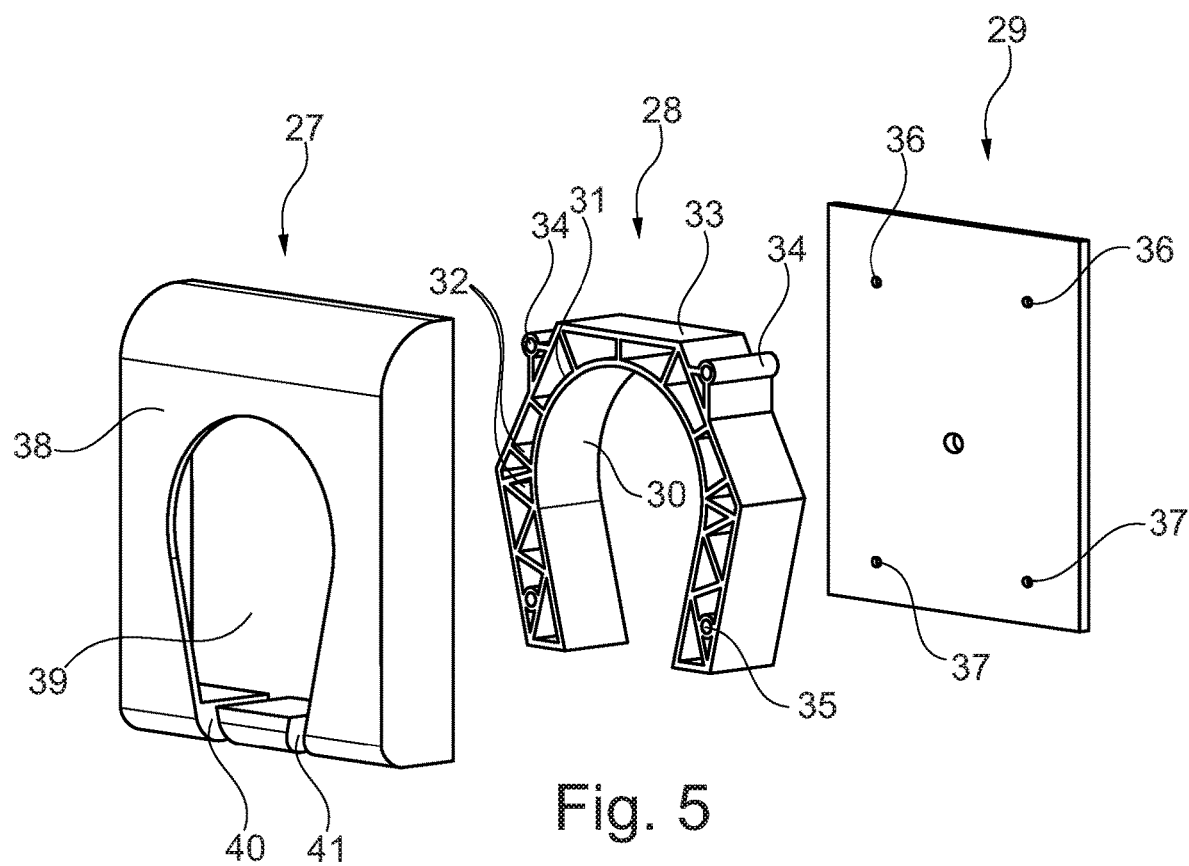
FIG. 5 shows the supporting surface module of FIGS. 3 and 4 comprising a casing module adapted to be combined therewith and a mounting module adapted to be combined therewith.

In FIG. 5 seats 36, 37 of the mounting module 29 constituting interfaces are indicated. The interfaces of the casing module 27 are not evident from FIG. 5, as they are covered by a front wall 38 forming a cover. In the latter, a central recess 39 is formed through which the rotor 18 as well as an elastically deformable fluid line 22 arranged between the rotor 18 and the supporting surface 30 and not shown in the Figures are visible. FIG. 5 indicates that the casing module 27 includes adapters 40, 41 for the blood lines 1, 4 as further functional units. The fluid line 22 is deformed upon rotation of the rotor 18. It is connected to the arterial blood line 1 on the inlet side, namely, on the low-pressure side, and to the high-pressure blood line 4 on the outlet side, namely, on the high-pressure side. It is deformed between the rotor 18 and the supporting surface 21 so that during faultless normal operation of the pump its cross-section is preferably completely pinched off, namely, is closed in a substantially fluid-tight manner.

The invention claimed is:

1. A peristaltic pump of an apparatus for extracorporeal blood treatment for delivering fluid in the apparatus, the peristaltic pump comprising:
    a rotor driven to rotate about a rotor axis; and
    a pump casing surrounding the rotor at least in part, the pump casing:
        having a supporting surface which is configured to be curved around the rotor axis of the rotor,
        having a modular design and including at least a first supporting surface module configuring the supporting surface and at least a second casing module adapted to be coupled to the first supporting surface module and at least partly surrounding or receiving the rotor, the first supporting surface module comprising at least one standardized interface for coupling to at least one of the second casing module, a mounting module, or a casing element of the apparatus;
    wherein an elastically deformable fluid line is adapted to be positioned between the rotor and the supporting surface and is deformed between the rotor and the supporting surface such that a cross-sectional constriction delivers fluid by rotation of the rotor.

2. The peristaltic pump according to claim 1, wherein the pump casing includes the mounting module which is adapted to be coupled to at least one of the supporting surface module or to the casing module and is adapted to be coupled to the apparatus for extracorporeal blood treatment.

3. The peristaltic pump according to claim 1, wherein the mounting module is adapted to be coupled to a casing of the apparatus.

4. The peristaltic pump according to claim 1, wherein the second casing module comprises a standardized interface for coupling to at least one of the first supporting surface module, the mounting module, or a casing element of the apparatus.

5. The peristaltic pump according to claim 1, wherein the mounting module comprises a standardized interface for coupling to at least one of the first supporting surface module, the casing module, or a casing element of the apparatus.

6. The peristaltic pump according to claim 1, wherein a plurality of supporting surface modules is provided which are different from each other with respect to at least one of the radius of their supporting surface or the wrapping angle formed by their supporting surface.

7. The peristaltic pump according to claim 1, wherein a plurality of casing modules is provided which are different from each other with respect to at least one of their fluid line adapter, their equipment interface with sensors, a cover adapter, or the design.

8. The peristaltic pump according to claim 1, wherein the first supporting surface module is an extrusion-molded element or a deep-drawn element or is formed by cold forming.

9. The peristaltic pump according to claim 1, wherein the first supporting surface module is an extruded plastic component, an injection-molded component, or a mechanically machined metal part.

10. The peristaltic pump according to claim 1, wherein the mounting module is in the form of a separate component or is part of a casing of the apparatus.

11. The peristaltic pump according to claim 1, wherein the supporting surface module is made from a metallic material or from a plastic material.

12. The peristaltic pump according to claim 1, wherein the apparatus is a dialysis machine.

13. An apparatus for extracorporeal blood treatment comprising a peristaltic pump according to claim 1.

* * * * *